United States Patent
Hoecht et al.

(10) Patent No.: US 11,627,927 B2
(45) Date of Patent: Apr. 18, 2023

(54) MEDICAL IMAGING DEVICE HAVING A MOVABLE PATIENT COUCH AND A TOUCH-SENSITIVE AND FORCE-SENSITIVE INTERFACE FOR CONTROLLING THE MOVABLE PATIENT COUCH, AND METHOD FOR OPERATING A MEDICAL IMAGING DEVICE

(71) Applicant: Siemens Healthcare GmbH, Erlangen (DE)

(72) Inventors: Philipp Hoecht, Lauf (DE); Felix Wolf, Erlangen (DE)

(73) Assignee: Siemens Healthcare GmbH, Erlangen (DE)

( * ) Notice: Subject to any disclaimer, the term of this patent is extended or adjusted under 35 U.S.C. 154(b) by 734 days.

(21) Appl. No.: 16/662,686

(22) Filed: Oct. 24, 2019

(65) Prior Publication Data
US 2020/0129134 A1 Apr. 30, 2020

(30) Foreign Application Priority Data
Oct. 24, 2018 (EP) .................................... 18202333

(51) Int. Cl.
*A61B 6/00* (2006.01)
*A61B 6/03* (2006.01)
(Continued)

(52) U.S. Cl.
CPC .............. *A61B 6/467* (2013.01); *A61B 5/055* (2013.01); *A61B 6/032* (2013.01); *A61B 6/0407* (2013.01);
(Continued)

(58) Field of Classification Search
CPC ........... A61B 6/03; A61B 6/032; A61B 6/035; A61B 6/037; A61B 6/04; A61B 6/0407;
(Continued)

(56) References Cited

U.S. PATENT DOCUMENTS 8,599,142 B2 * 12/2013 Prados .................... G06F 3/016
345/173
8,860,677 B2 * 10/2014 Dörre ...................... G06F 3/016
340/407.1
(Continued)

FOREIGN PATENT DOCUMENTS

DE 102009036860 A8 6/2011
DE 102010064056 A1 6/2012
(Continued)

OTHER PUBLICATIONS

An English translation of EP 3 348 201 A1 by Patent Translate. (Year: 2022).*
(Continued)

*Primary Examiner* — Allen C. Ho
(74) *Attorney, Agent, or Firm* — Banner & Witcoff Ltd.

(57) ABSTRACT

A medical imaging device, such as a computed tomography device and/or a magnetic resonance device, includes at least one movable component. The at least one movable component can include a patient couch, and the medical image device can further include an operating device for controlling the operation of the at least one component. The operating device can include a touch-sensitive and force-sensitive interface (e.g. touchscreen display) having at least one touch sensor and at least one force sensor that measure the strength of a touch.

19 Claims, 3 Drawing Sheets

(51) Int. Cl.

| | | |
|---|---|---|
| *A61B 6/04* | (2006.01) | |
| *G16H 30/20* | (2018.01) | |
| *G06F 3/041* | (2006.01) | |
| *G01R 33/30* | (2006.01) | |
| *G01T 1/161* | (2006.01) | |
| *G05B 15/02* | (2006.01) | |
| *G06F 3/044* | (2006.01) | |
| *A61B 5/055* | (2006.01) | |

(52) U.S. Cl.
CPC ............ *A61B 6/0487* (2020.08); *A61B 6/461* (2013.01); *A61B 6/469* (2013.01); *A61B 6/54* (2013.01); *G01R 33/307* (2013.01); *G01T 1/161* (2013.01); *G05B 15/02* (2013.01); *G06F 3/044* (2013.01); *G06F 3/0416* (2013.01); *G06F 3/04142* (2019.05); *G16H 30/20* (2018.01)

(58) Field of Classification Search
CPC .......... A61B 6/0487; A61B 6/08; A61B 6/10; A61B 6/102; A61B 6/44; A61B 6/4429; A61B 6/4435; A61B 6/4441; A61B 6/4447; A61B 6/46; A61B 6/461; A61B 6/462; A61B 6/465; A61B 6/467; A61B 6/469; A61B 6/54; A61B 6/542; A61B 6/545; A61B 6/547; A61B 5/0033; A61B 5/0035; A61B 5/055; A61B 2090/374
USPC ....... 378/4, 20, 91, 98, 196–198, 209; 5/601
See application file for complete search history.

(56) References Cited

U.S. PATENT DOCUMENTS

| | | | | |
|---|---|---|---|---|
| 9,462,981 | B2* | 10/2016 | Padwa | A61B 6/0492 |
| 9,851,708 | B2* | 12/2017 | Heijman | H03K 17/962 |
| 10,061,413 | B2* | 8/2018 | Fink | G06F 3/041 |
| 10,182,784 | B2* | 1/2019 | Karl | A61B 6/4494 |
| 10,303,355 | B2* | 5/2019 | Beckmann | A61B 5/055 |
| 10,379,692 | B2* | 8/2019 | Greif | G06F 3/04186 |
| 10,459,624 | B2* | 10/2019 | Wellhöfer | A61B 3/0033 |
| 10,492,753 | B2* | 12/2019 | Kagermeier | G06T 7/246 |
| 10,966,680 | B2* | 4/2021 | Kagermeier | G16H 30/20 |
| 10,973,591 | B2* | 4/2021 | Schweizer | A61B 6/465 |
| 11,016,571 | B2* | 5/2021 | Trapp | B60K 37/06 |
| 11,020,022 | B2* | 6/2021 | Hao | A61B 6/04 |
| 11,298,099 | B2* | 4/2022 | Ten Cate | A61B 5/6889 |
| 2012/0188187 | A1 | 7/2012 | Dorre et al. | |
| 2015/0277420 | A1 | 10/2015 | Heijman et al. | |
| 2016/0162081 | A1 | 6/2016 | Greif et al. | |
| 2016/0278728 | A1 | 9/2016 | Karl et al. | |

FOREIGN PATENT DOCUMENTS

| | | |
|---|---|---|
| DE | 102011089672 A1 | 6/2013 |
| DE | 102012207114 A1 | 6/2013 |
| DE | 102012201379 A1 | 8/2013 |
| DE | 102009036941 B4 | 3/2014 |
| DE | 102014225235 A1 | 6/2016 |
| DE | 102015204767 A1 | 9/2016 |
| DE | 102015205286 A1 | 9/2016 |
| DE | 102015205285 B4 | 2/2017 |
| EP | 3348201 A1 | 7/2018 |

OTHER PUBLICATIONS

An English translation of DE 10 2015 204 767 A1 by Patent Translate. (Year: 2022).*
Harald Karl et al., Secure touch evaluation in resistive touch elements by way of additional capacitive measurement by using the resistive structures.
Goran Grbic, Jim Morrison, Daniel Yang and Darko Veselinovic: "Force Touch Technology—An Intellectual Property Perspective"; Chipworks; Sep. 2015; http://www.chipworks.com/about-chipworks/overview/blog/force-touch-technology-intellectual-property-perspective; 2015.
ICEI IEC 62304; International Standard, First edition; May 2006; "Medical device software—Software life cycle processes", Reference No. CEI/IEC 62304:2006.
Harald Karl et al., Monitoring the integrity of a representation on a display by means of evaluation of specific location, color and pattern information.
European Search Report dated Apr. 4, 2019, Application No. 18202333.3.

* cited by examiner

MEDICAL IMAGING DEVICE HAVING A MOVABLE PATIENT COUCH AND A TOUCH-SENSITIVE AND FORCE-SENSITIVE INTERFACE FOR CONTROLLING THE MOVABLE PATIENT COUCH, AND METHOD FOR OPERATING A MEDICAL IMAGING DEVICE

CROSS REFERENCE TO RELATED APPLICATIONS

This patent application claims priority to European Patent Application No. 18202333.3, filed Oct. 24, 2018, which is incorporated herein by reference in its entirety.

BACKGROUND

Field

The disclosure relates to a medical imaging device, in particular to a computed tomography device and/or a magnetic resonance device having at least one component able to be moved by means of an actuator and/or able to be adjusted by means of an adjustment means, an operating device for controlling the operation of the at least one component and a controller assigned to the operating device. As well as this, the disclosure relates to a method for operating such a medical imaging device.

Related Art

Medical imaging devices, in particular larger systems such as magnetic resonance devices and/or x-ray devices, usually have components that are able to be moved or adjusted respectively via actuators and/or via means of adjustment. An example of this type of component is a patient couch, which can be moved into a gantry and/or patient receiving area for example. With x-ray devices in particular further movable components can also exist, for example parts of the recording arrangement and/or carrier elements, for example a C-arm in an x-ray device with a C-arm as its medical imaging device. Examples of adjustable components include lighting components, which can be able to be adjusted in their brightness, air-conditioning devices, for example fans, which can be able to be adjusted in their intensity, and the like. Naturally there can also be components present that are movable and adjustable.

It is a peculiarity of medical imaging devices here that, when carrying out an operating action, an operator is mostly not looking at the operating device or in concrete terms at a corresponding means of operation, but at the component to be operated. With a patient couch for example the operator is looking to make sure that the safety of the patient supported thereon is guaranteed and that the target position is correctly reached. This results in diverse requirements on operating devices of medical imaging devices.

Nonetheless it has also been proposed in the interim that a touchscreen (touch display) be used as well as other means of operation as a means of operation of an operating device for medical imaging devices, for example magnetic resonance devices. While in other areas full attention is paid to the touchscreen during the operation of a touchscreen, for example with smartphones, tablets and ATMs, during the operation of a medical imaging device the operator's attention is on the patient or the component respectively, so that functionalities, such as for example moving the patient couch, should ideally be able to be possible "blind", which means at least primarily keeping one's eyes on the patient and/or the component. This is not readily possible with buttons, controls and/or other operating elements realized via touchscreens, so that further means of operation/operating units are employed.

Thus, for conventional magnetic resonance devices for example, means of operation in a fixed geometrical arrangement and with haptic feedback given during actuation of an operating element have been proposed for operation of movable and/or adjustable components. An actual, known embodiment makes provision for example for using means of operation with a number of, partly two-stage, short-travel buttons and/or rotary wheels with return springs ("jogwheel"). In this case haptic feedback exists for example when a short-travel button is pressed and also when a rotary wheel is deflected, so that the medical imaging device is able to be operated with a little practice without being looked at or with just a brief glance at the means of operation.

As regards the use of touchscreens it has been proposed that a structuring be introduced into the glass surface of the touchscreen, for example providing hollows and/or raised areas, which can be "located by touch" to realize specific functions, for example the moving of the patient couch, or can be operated "blind" as a result of the guidance in a hollow. However in such cases there is the disadvantage of being constrained to a specific function at a specific point on the touchscreen. It is further hard to distinguish between specific functionalities and the layout and manufacture become more complex.

Another special requirement to be noted in the design of operating devices for medical imaging devices is the high level of safety necessary in respect of the patient. This applies in particular for patient couches and/or other moving components. For moving components, in particular for patient couches, different realizations of movement options have been proposed in such cases, for example travel to a destination (ZF), in which a command for a specific destination is specified as an operating action, and continuous travel (KF), in which movement is until such time as the operating element assigned to a movement is released again. In such cases, as already explained, mechanical operating elements, for example short-travel buttons and rotary wheels with return springs are mostly explicitly used.

To ensure an error-free operation, for patient couches in particular, a few measures for operating devices have already been proposed. Thus for example mechanically provided stop switches can be of a single fault safe design for ending the movement for movable components, in particular patient couches, i.e. in particular through redundant actuation detection. Single fault safety in such cases is in particular understood as no first fault being able to cause an unacceptable risk for the patient.

For operating elements to which travel to a destination is assigned there can be provision for example for pressing the corresponding operating element for a specific period of time, before the corresponding journey to the destination is initiated. In this way an accidental triggering is avoided. For continuous travel of components it has been proposed that a type of "dead man's handle" be realized, meaning that a travel command is sent continuously for as long as the assigned operating element is actuated. Likewise specific software safety classes that can be implemented are provided for the firmware of the operating devices.

A single fault safe touchscreen for medical imaging devices has in fact already been proposed, which uses two touch sensors, namely a resistive and also a capacitive touch sensor. For an example of this the reader is referred to DE 10 2012 207 114 A1.

BRIEF DESCRIPTION OF THE DRAWINGS/FIGURES

The accompanying drawings, which are incorporated herein and form a part of the specification, illustrate the embodiments of the present disclosure and, together with the description, further serve to explain the principles of the embodiments and to enable a person skilled in the pertinent art to make and use the embodiments.

Figure 1:
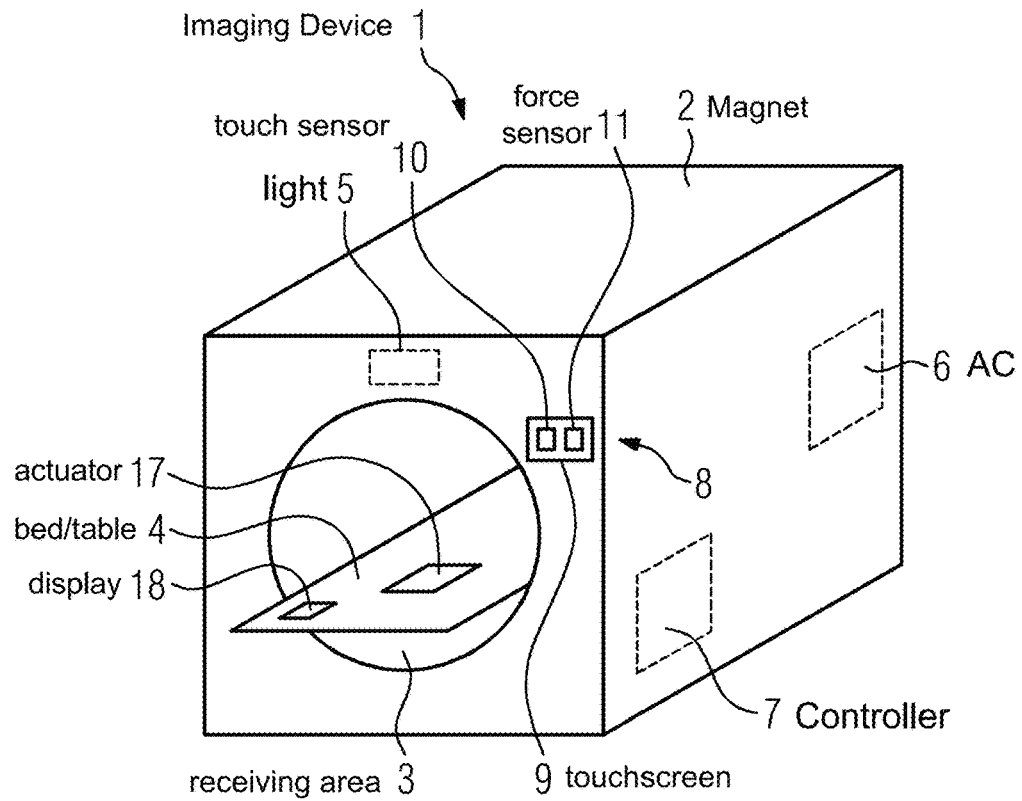
FIG. 1 is a schematic illustration of a medical imaging device according to an exemplary embodiment.

The exemplary embodiments of the present disclosure will be described with reference to the accompanying drawings. Elements, features and components that are identical, functionally identical and have the same effect are—insofar as is not stated otherwise—respectively provided with the same reference character.

DETAILED DESCRIPTION

In the following description, numerous specific details are set forth in order to provide a thorough understanding of the embodiments of the present disclosure. However, it will be apparent to those skilled in the art that the embodiments, including structures, systems, and methods, may be practiced without these specific details. The description and representation herein are the common means used by those experienced or skilled in the art to most effectively convey the substance of their work to others skilled in the art. In other instances, well-known methods, procedures, components, and circuitry have not been described in detail to avoid unnecessarily obscuring embodiments of the disclosure.

An object of the disclosure is to specify an improved option for realizing a touch-sensitive means of operation relating to the safety and/or operability of a medical imaging device.

In a medical imaging device of the type stated at the outset there is provision in accordance with the disclosure for the operating device to have a touch-sensitive and force-sensitive, flat means of operation having at least one touch sensor and at least one force sensor measuring the strength of the touch.

In other words it is thus proposed that a so-called force-touch means of operation be used as part of the operating device, by means of which both touches on the operating surface of the means of operation can be established and also the strength of said touches as a touch force, to which end a force sensor is used in addition to a touch sensor. In this case the term "force sensor" is to be broadly understood as a sensor that records measurement data describing a force. As well as "classical" force sensors, examples also include acceleration sensors, deflection sensors, which detect the deflection of a spring element for example, and the like.

In an exemplary embodiment, the controller is configured to evaluate sensor data of both the touch sensor and also of the force sensor, in order to be able to establish operating actions and to bring about a corresponding activation of the actuators and/or means of adjustment as well as other elements of the medical imaging device if necessary. In this case the means of operation preferably has a plate, in particular a glass plate, as its operating surface. The plate can be assigned the force sensor embodied as a piezo sensor and/or strain gage for example, wherein mostly a number of force sensors are used, to also enable a touch position measurement to be carried out by means of the force sensors. The touch sensor can be designed as a capacitive touch sensor for example. A touch force measurement can also be made, taking into account a change in capacitance.

A specific embodiment with an essentially rectangular plate can provide for a force sensor, in particular a piezo element, being provided in each corner of the plate in each case, so that as a result of the different forces entered into the different force recorders (i.e. force sensors) not only can an evaluation result describing the overall strength of the touch be obtained, but as a result of the distribution of the forces entered, a position of the touch result can be geometrically determined as a "force event".

The provision of force-touch means of operation as part of the operating device firstly makes it possible to enhance safety in the adjustment and/or movement of components, secondly to also allow components to be operated via correspondingly implemented operating actions without looking at the means of operation, and finally to enhance the flexibility in relation to possible operating actions, since with the strength of the touch measured with the force sensor, a further parameter characterizing the operating actions is present. Actual implementations of these described advantages will be explained in greater detail below. Since the means of operation in particular can be realized as a touchscreen (with a display device built in as a display) and moreover with "blind" operability via the means of operation, no further operating elements/means of operation, for example haptically palpable and/or haptic elements responding mechanically are necessary on the operating device, there can be complete operation of the medical imaging device via the means of operation embodied in particular as a touchscreen. Contact with the patient is improved in that the means of operation can be operated without looking at said means. Doing away with further means of operation or operating elements can further lead to cost savings, since only a small additional premium is necessary through the embodiment of a touch means of operation as a force-touch means of operation.

The disclosure may relate to mobile components of the medical imaging device, in particular to the patient couch and/or other components able to be moved in the area of the patient. It is also able to be used to advantage however with other components that are accessible for movement and/or adjustment by means of the operating device, for example lighting components, air conditioning components such as fans, and the like.

In an exemplary embodiment, to enhance operating safety, there can be provision in accordance with the disclosure for the force sensor and the touch sensor to each be assigned their own controller and/or for the controller configured to detect at least one possible operating action, in particular related to the movement of a component only for touch position data of the touch sensor, in particular matching within a tolerance range and of a force sensor embodied at least for touch position measurement and/or only when a minimum touch force and/or a minimum touch period is exceeded. In such cases, as already explained, it is especially preferred that a number of force sensors built-in at different positions of the flat means of operation be provided for force sensor-side touch position measurement, the measured part forces of which are evaluated in each case in the assigned controller and/or the controller to establish a touch position and a touch force.

In particular in respect of a redundant touch position measurement it is thus possible, in a similar way to known touchscreens using capacitive and resistive touch sensors, to establish a single fault safety at least as regards selected operating actions assigned to the safety of the patient, in that the redundant determination is utilized and a comparison is made, wherein only when the touch positions, in particular within a tolerance range, match, can a corresponding operating action actually be assumed. In this way for example incorrect initiations caused by measurement errors or the like can be counteracted. This is further supported by the independent evaluation of the raw data of the touch sensor and of the force sensor in independent controllers, wherein an independent evaluation on its own is also expedient. Especially advantageously in addition to a utilization of the redundancy for a touch position measurement, as further conditions for at least some of the operating actions, in particular operating actions assigned to the movement of components, specific, in particular further, requirements can also be imposed. For example there can be a requirement for a certain minimum force to be exceeded in order to be able to recognize an operating action, so that light, accidental touches do not represent an operating action and thus do not initiate any control measure.

In the example of a patient couch as a component, movements of the patient couch are thus only initiated when all conditions are met. For example, with the Continuous Table Movement (CTM) travel mentioned at the outset, movement commands can be sent continuously for as long as the conditions for the assigned operating action are met. With CTM travel the corresponding operating actions can also be assigned additional conditions, for example compared to CTM travel, for example the exceeding of a certain period of time for which the operations must be kept to. Such a minimum touch period can amount to 0.8 to 2 seconds, preferably to 1 second. In addition to the conditions given by way of example, which can be assigned separately to different operating actions, further conditions are naturally also conceivable, which can also express themselves in the operating actions, but which further enhance the operating safety. For example, operating actions for critical movements and/or adjustments can be comprehensively requested explicitly as multi-touch/force-operating actions and/or specific gestures, i.e. movements on the operating surface. Requiring multi-touch/force events as an operating action can also be understood as a kind of "safe touch", which means that an operating element hitherto realized as a separate, additional means of operation, which was required in addition to an operation via a touchscreen for example, can be done away with if the redundant design of the means of operation, specifically of the touchscreen, can be ensured.

As already mentioned, the additional determination of the force of the touch by the force sensor allows further expedient functionalities. There can thus be provision for example for the controller configured to adapt (e.g. step-less adapt) at least one control parameter assigned to an operating action, in particular a speed of movement, as a function of the touch force measured for the operating action. The use of a force-touch means of operation thus allows the stepless variation of a variable, for example the speed of movement of a patient couch, dependent on the force with which the means of operation is pressed.

It is also especially advantageous with aspects of the present disclosure for the controller configured to distinguish between operating actions as a result of a touch force and/or touch duration and/or to recognize a double touch occurring within a period of time as an operating action, in particular for switching a mode of operation. For these embodiments in particular it is true to say that, for identification of a touch action as an operating action to which a control measure is assigned, the touch position can naturally additionally be taken into account, for example for assigning it to an operating area of the operating surface of the means of operation.

For example operating actions can thus also be distinguished depending on the force exerted during the touch, which is only expediently made possible by the provision of a force sensor and thus makes possible a better differentiation of operating actions/a greater number of different operating actions, only precisely in conjunction with the consideration of an operating duration. Especially expediently the recognition of a double touch occurring within a period of time can be recognized as an operating action, since in this way a kind of "double click" can be realized via the means of operation, which in particular can expediently be employed for choosing specific modes of operation without glancing at the means of operation. For example such a "double click" can lead to the activation of a mode of operation for moving a specific component, in particular a patient couch.

In an especially advantageous embodiment of the present disclosure there is provision for the controller configured to evaluate the course of the touch force over time for detection of an operating action. This means that a time-force curve is analyzed in order to be able to establish specific operating actions and in particular to be able to distinguish them from other operating actions, which have other touch force curves over time. An especially preferred specific embodiment in this context makes provision for the controller configured to detect an emergency operating action, in particular an emergency movement stop, with a pulse-like touch force curve, in which a touch force exceeding a force threshold value is reached with an increase exceeding an increase threshold value and/or in a time falling below a time threshold value. A pulse-type touch force curve of this type arises for example when the operator strikes the operating surface of the means of operation, in particular also a larger surface. This type of "hard impact" can be recognized by the controller and assigned to an emergency control measure, for example an emergency movement stop. In this way an emergency operating element can also be provided by the means of operation.

In an exemplary embodiment of the present disclosure, the controller is configured to detect at least one first operating action, depending on the touch position of the operating action, to define at least two operating areas of the operating surface of the means of operation in which second operating actions assigned to different functionalities in each case are able to be detected. This embodiment especially advantageously makes possible a spatial decoupling of the operating activity from predetermined positions on the operating surface of the means of operation. This is since ultimately a first operating action able to be carried out especially advantageously without looking is sufficient in order to activate a mode of operation, in which the dynamic operating areas are created that are assigned to specific functionalities and the location of which is certainly known to the operator since the touch position of the first operating action is known to them. Thus there is still no need to look. If a display facility is provided, i.e. for example the means of operation is embodied as a touchscreen, a display of the display facility can also be adapted so that the corresponding operating areas are described, in order to enable the means of operation itself to give optical feedback. In other words this means that for example a specific graphical overlay and/or another display representation can be shown when the first operating action is carried out at the given operating surface, i.e. the touch position of the first operating action, which is or are tailored respectively to just this touch position and the operating areas defined by said position.

In a specific embodiment of this especially preferred development there can be provision for at least two opposite operating areas to be assigned to the activation of different directions of movement and/or directions of adjustment of one of the at least one components, in particular of the patient couch, in relation to the touch position of the first operating action by the controller, wherein in particular the touch force of a second operating action provided for moving the component on the controller side is able to be evaluated to establish a speed of movement and/or speed of adjustment. Thus for example if the first operating action, in particular pressing on a given touch position with a prespecified touch force and/or touch duration, is carried out, the movement of a component can be activated, wherein for example an operating area provided in a direction starting from the touch position can be used for movement in one direction, the other, opposite operating area for movement in an opposite direction by corresponding second operating actions. In this case such an embodiment is not restricted to the movement of components however, but can also relate to other components able to be adjusted in other ways, for example to increasing or reducing the level of light of an illumination component and/or the fan flow of an air conditioning component.

It is also especially advantageous in this context for the controller configured to choose/select an operating area by evaluating the direction of a dragging action starting from the touch position after the first operating action. For example a second operating action can thus follow on directly from the first operating action, by a finger carrying out the operation for example being moved on from the touch position into an operating area that can be selected on the basis of this direction.

An operating concept can thus be produced within the framework of the present disclosure precisely in conjunction with the options described above for the definition of first operating actions that activate specific modes of operation, in which for example, starting from a means of operation that is in an idle mode, different first operating actions can lead to different operating modes with operating areas having a different effect and/or predetermined operating areas depending on the touch position. For example it is thus conceivable, via a "double click", thus a double touch taking place within a period of time, as a first operating action for an operating mode for moving a prespecified component, for example the patient couch, to be activated. Here for example at least two operating areas, for example "upwards" and "downwards" from the touch position can be defined, which can be assigned a movement of the patient couch upwards and/or into a patient receiving area/gantry or downwards and/or out of a patient receiving area/gantry. Naturally further operating areas can also be defined, for example an operating area "to the left", which leads to a movement of the patient couch into a basic position and/or an operating area "to the right", which activates a laser positioning aid for the patient couch. Second operating actions within the corresponding operating areas then lead to corresponding reactions, i.e. to the carrying out of control measures assigned to the respective action of the second operating actions. If for example the operating mode for moving the patient couch is selected, for example by the "double click" mentioned or by touching the touch position with a specific touch force and/or touching it for a specific period of time, the finger can be moved on into an operating area where a movement with a speed of movement corresponding to the touch force can be initiated and the like. It should be pointed out that the first operating action or also other types of operating action are of course conceivable as the second operating action, for example force-touch gestures, L-shape gestures, multi-touch gestures and the like.

In the stated example just discussed other first operating actions starting from the idle mode can also be provided, for example for activating a patient comfort mode, wherein operating areas correspondingly defined as a function of the touch position can then serve to adjust an air conditioning component, for example a patient fan, and/or a lighting component, wherein one of these components given by way of example is then in particular assigned two opposite operating areas as regards the touch position in each case, for example "up/down" to the lighting component, "left/right" to the air conditioning component.

The combination of the options described above thus enables especially advantageous operating actions or sequences of operating actions to be defined, in particular able to be carried out without looking at the means of operation. For example an embodiment is also conceivable wherein, by pressing on the operating surface with a touch force exceeding a prespecified minimum touch force as the first operating action, then continuing the movement of the touching finger into an operating area and pressing there with a touch force, the movement of a movable component is selected and then the component is moved with a speed of movement corresponding to the touch force by activation of the actuator by means of the controller.

In an expedient development there can be provision for the operating device to have at least one acoustic and/or haptic and/or optical display means assigned to the means of operation, for displaying and/or acknowledging at least one operating action. This means that acoustic, haptic and/or optical feedback can be given, which is suitable in particular for supporting "operation without looking". While with some operating actions the feedback can be recognized directly by the movement and/or adjustment of the corresponding component, for example when the patient couch starts to move, a lighting component is switched on or the like, with other operating actions resulting in control measures for components, it can be less obvious that the control measure has been carried out or that the operating action has been recognized. To this end for example haptic feedback, for example through a vibration facility on the means of operation itself can be expedient, wherein acoustic display means are also expedient, since they can be perceived without the operator having to look, for example loudspeakers or the like. Especially advantageous in respect of haptic display means is one comprising the embodiment of the force sensors as piezo elements; the force sensors can then be used simultaneously as a haptic display means. However optical display means are also able to be employed, wherein a preferred development makes provision for the optical display means to be assigned to at least one component and to be arranged in the field of vision of a person using the means of operation for the component and/or a patient, remote from the means of operation. This means that optical display means can also be arranged remote from the means of operation in the assumed field of vision of operator, so that this expedient field of vision of the person using the means of operation does not have to be altered and it is still made possible for optical feedback advantageously to be given.

As already mentioned, expedient forms of embodiment of the present disclosure can make provision for the means of operation to have a display device at least partly covering the operating surface, in particular the means of operation is embodied as a touchscreen. Touchscreens that also have force sensors, as a "force-touch display" for example, have already become widely known in the prior art, in respect of tablets and/or smartphones for example. In such cases a touchscreen has the advantage, even by comparison with a prior art touchscreen having a number of touch sensors, in concrete terms a resistive and a capacitive touch sensor, likewise contributing to operating safety, that "force touch", that is the embodiment with a touch sensor and a force sensor, by contrast with the touchscreen using two touch sensors, does not adversely affect the image quality of the display on the touchscreen. A further advantage of a touchscreen that additionally has at least one force sensor is that ultimately the software for such approaches already exists, thus savings can also be made here. Touchscreens have the further advantage that they can also be employed in an especially simple manner for undertaking further operating actions not needing attention to the component and/or the patient, in which the operator can, possibly has to, concentrate fully on what is being displayed on the touchscreen. An example of this is setting recording parameters for an impending imaging process of the medical imaging device. The means of operation provided by the disclosure is thus sufficient for carrying out all necessary operating actions at the medical imaging device, without further means of operation of the operating device absolutely having to be providing. The result of this is an operating device that is simplified, intuitive and can be implemented at low cost.

It should be pointed out that these types of display devices, which are assigned to the operating surface, can also be realized in other ways, for example as LED arrays and the like.

In an exemplary embodiment, when a touchscreen is used as the display device, an especially advantageous development of the present disclosure makes provision that, when there is provision for the dynamic definition of operating areas for at least one first operating action, the controller is configured to activate the display device for display of information describing the operating areas. This means that, when the first operating action is carried out, the operating areas can also be optically indicated around the touch position, for example by the display of corresponding operating elements. In this way the operator still taking a brief glance at the means of operation can make sure quickly and easily that they have correctly activated the operating mode activated by the first operating action. Moreover a corresponding display of the information describing the operating areas provides a kind of help function, in particular for new operators. In this way a flexible design of the user interface is provided as well at the same time, since ultimately no there is no stipulation as to physical or physically permanently defined operating elements, but depending on the touch position, operating areas dynamically adapted to the operating mode required by the corresponding first operating action can be created or adapted.

The medical imaging device, as has already been explained, can involve an x-ray device, in particular a computed tomography device and/or a magnetic resonance device. In concrete terms there can be provision here for example, with a medical imaging device embodied as a computed tomography device, for the means of operation to be arranged on a gantry and/or with a medical imaging device embodied as a magnetic resonance device, for the means of operation to be arranged adjacent to a patient receiving area on a main magnet unit. Normal, meaning non-force-sensitive, touchscreens have already been proposed at these positions, so that the position is also suitable for the means of operation described here. Naturally other positions are also conceivable for the means of operation, for example adjacent to a patient couch.

One of the at least one components is preferably a patient couch, since with medical imaging devices such couches are frequently controlled via a motor as an actuator of movable patient couches and moreover, when the patient couch is moved with the patient positioned thereon, the operator's attention also has to be on said couch. Further components, in particular those provided in addition to the patient couch can include an imaging component and/or a carrier component and/or a lighting component and/or an air conditioning component, for example a patient fan. For example with x-ray devices with a C-arm, carrier elements also exist, in particular the C-arm itself, and/or imaging components, for example x-ray emitter and/or x-ray detector, which can be configured such that they can be moved via the operating device and, in particular with a conceivable danger of collision with a patient, during which an eye has to be kept on control via the operating device. The inventive embodiment is also especially suitable for these types of components.

As well as the medical imaging device, the present disclosure also relates to a method for operating a medical imaging device, in particular a computed tomography device and/or a magnetic resonance device, wherein the imaging device has at least one component able to be moved by means of an actuator and/or able to be adjusted by means of an adjustment means, in particular comprising at least a patient couch, an operating device for controlling the operation of the at least one component and having controller assigned to the operating device. In such a method there is provision in accordance with the disclosure for a touch-sensitive and force-sensitive flat means of operation having at least one touch sensor at least one force sensor measuring the strength of the touch to be used as the means of operation of the operating device. Everything that has been stated in relation to the inventive imaging device can be transferred analogously to the inventive method, so that the advantages already given can also be obtained with said method. In particular the controller of the medical imaging device can be embodied to carry out the inventive method.

FIG. 1 shows a medical imaging device 1 in accordance with an exemplary embodiment of the present disclosure, where the medical imaging device 1 is a magnetic resonance device. In this example this has a main magnet unit 2, as is basically known in the prior art, and in particular accommodates the basic field magnet of the magnetic resonance device. The main magnet unit 2 defines a cylindrical patient receiving area 3, into which a patient couch 4 can be moved as a movable component of the medical imaging device 1. In this context the medical imaging device 1 can further have a lighting component 5 for illuminating the interior of the patient receiving area 3 and an air conditioning component 6, for example a patient fan. The operation of the medical imaging device 1 is controlled by means of a controller 7. To enable components, for example the patient couch 4, the lighting component 5 and/or the air conditioning component 6, to be moved and/or adjusted manually, the medical imaging device 1 further has at least one operating device 8, to which the controller 7 is assigned and which in the present example involves a flat means of operation 9 embodied as a touchscreen, which is not only touch-sensitive but is also force-sensitive, so that it involves a force-touch means of operation 9. The means of operation 9 thus has a touch sensor 10 as well as at least one force sensor 11. This enables not only the presence and the position of touches on the operating surface of the means of operation 9 to be determined, but also their strength. In an exemplary embodiment, the controller 7 includes processor circuitry that is configured to perform one or more operations and/or functions of the controller 7, including controlling the medical imaging device 1.

Figure 2:
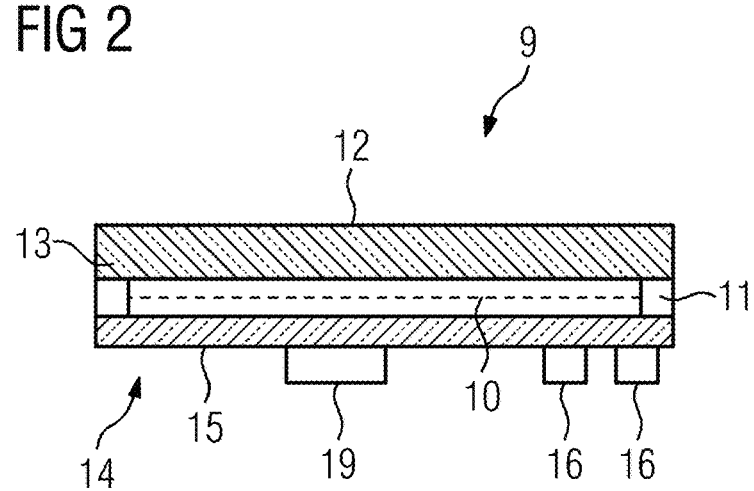
FIG. 2 is a schematic cross-sectional view of a touchscreen according to an exemplary embodiment.

FIG. 2 shows a schematic of the structure of the means of operation (e.g. touchscreen) 9 according to an exemplary embodiment. This has a plate 13 defining the operating surface 12, in particular a glass plate, to which, as just indicated here and is basically known, the for example capacitively-measuring touch sensor 10 is assigned. A force sensor 11, embodied here as a piezo element, is provided at each of the four corners of the plate 13. The display 15 of the touchscreen serves here as the display device 14. In this example the means of operation 9 also has two controllers 16, of which one is assigned to the touch sensor 10 and one to the force sensors 11. This makes sure that the sensor data of the sensors 10, 11 is initially handled independently. The controllers 16 assigned to the force sensors 11 or the controller 7 respectively are further configured, as a result of the forces entered into the individual force sensors 11, not only to establish the strength of the touch, but also to deduce a touch position, so that the touch position is thus established redundantly both by the touch sensor 10 and also by the force sensors 11. In this way there can be a contribution to a functionally safe deign of the operating device, in that operating actions will only be detected for matching touch positions of the touch sensor 10 and the force sensor 11 within a tolerance range. In an exemplary embodiment, the touchscreen 9 (including one or more components of the touchscreen 9) includes processor circuitry that is configured to perform functions and/or operations of the touchscreen 9 (or one or more functions/operations of one or more respective components therein).

As will be explained in greater detail below, the operation of the means of operation 9 is designed to request movements and/or adjustments of components even without looking at the means of operation 9. If for example the patient couch 4 is to be moved under manual control by means of the actuator 17 merely indicated here, it is to be assumed that the operator is explicitly keeping their eyes on the patient couch 4 and on the patient positioned thereon. This can also relate to the adjustment of other components, for example the lighting component 5 and/or the air conditioning component 6.

In order, despite this, at least with control measures that are not obviously able to be recognized through the movement and/or adjustment of the respective component, to be able to display the successful detection and/or carrying out of an operating action assigned to a control measure on the means of operation 9, although the operator has not been looking at the display device 14, the medical imaging device 1 can further have other acoustic and/or haptic and/or optical display means 18, 19, wherein the display means 18 in the present example can also involve an optical display means, which is explicitly arranged in the field of vision of the operator onto the patient and the patient couch 4. The display means 19 can involve an acoustic and/or haptic display means 19. With a haptic display means 19 the operator feels the haptic feedback directly when using the means of operation 9—they can also perceive an acoustic feedback without looking away from the patient or the component.

Figure 3:
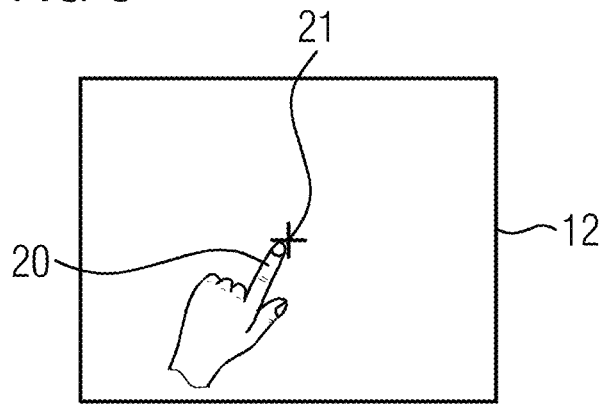
FIG. 3 shows a first operating action according to an exemplary embodiment.
Figure 4:
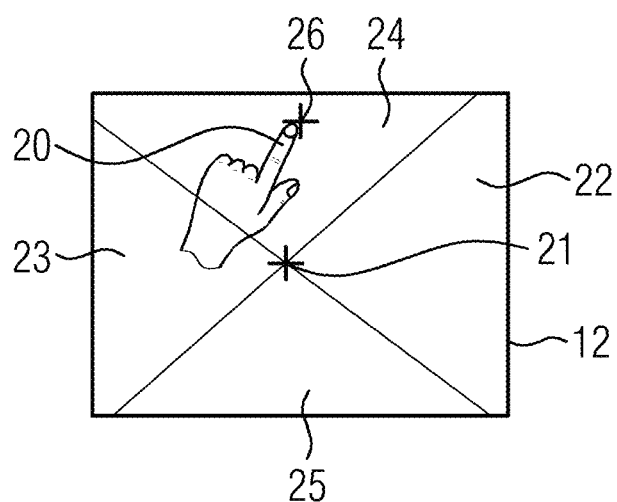
FIG. 4 shows a second operating action according to an exemplary embodiment.

FIGS. 3 and 4 explain a possible use of the means of operation 9 by means of the controller 7 in more detail. In these figures the means of operation 9 is in an idle mode for example before the events of FIG. 3, in which no display or a display explaining said device can be provided on the display device 15. By means of a finger 20, while continuing to keep their eyes directed to the patient and/or the component, the operator carries out a first operating action at a given touch position 21. So that the first operating action is even accepted as an operating action, a few safety queries are made in order to establish the single fault safety, in particular, whether a minimum touch force and/or a minimum touch duration are exceeded and whether both the touch sensor 10 and also the force sensors 11 within a tolerance range show the same touch position.

In this case different first operating actions, which are kept as simple as possible and relate explicitly to a given touch position 21, are conceivable, in order to activate different modes of operation, in particular modes of operation related to different components. For example the first operating action can comprise a "double click", i.e. a double touch taking place within a period of time and/or a lasting touch on the given touch position 21 present for at least a specific predetermined period and/or exceeding a predetermined touch force.

FIG. 4 shows the situation after first operating action at the given touch position 21. The operating surface 12 in this figure has been divided in this example into four operating areas 22, 23, 24, 25, wherein the operating areas 22 and 23 as well as 24 and 25 lie opposite one another in relation to the touch position 21. The operating areas 22 to 25 are shown by means of the display device 14 on the basis of dynamically generated information (not shown in any greater detail here on grounds of clarity), wherein the information not only contains the limits of the operating areas 22 to 25, but also their assignment, in order in particular to make it possible for new operators, by briefly glancing at the means of operation 9, to obtain operating help. An orientation has indeed already been given as a result of starting out from the touch position 21 of the first operating action.

If for example a movement of the patient couch 4 is to be controlled in the operating mode now activated, the operating areas 22 and 23 lying opposite one another can correspond in each case to a movement into and out of the patient receiving area 3; the upper and lower operating areas 24 and 25 likewise lying opposite one another can make it possible to control the height of the patient couch 4.

If the operator now undertakes a second operating action, as indicated with reference to the finger 20 shown once again and a further touch position 26 in the operating area 24, its effect is a result of the assignment to operating area 22 to 25. The strength of the touch for the second operating action detected by the force sensors 11 determines the speed of movement with which the controller 7, on detecting the second operating action, moves the patient couch 4, using the actuator 17 for example.

If, in the diagram shown in FIG. 3, another first operating action has been carried out at the given touch position 21, another operating mode can be activated, for example a patient comfort mode, in which the operating areas 22 to 25 can be assigned other functionalities, for example the operating areas 22 and 23 the adjustment of the strength of the air conditioning component 6 and the operating areas 24 and 25 the adjustment of the brightness of the lighting component 5.

As well as the examples described here, a plurality of other operating actions are of course also conceivable, to which a control measure of the controller 7 is assigned in each case, in particular gestures or force gestures, multi-touch operating actions and the like. In each case the controller 7 is also configured, in the exemplary embodiment shown here, to recognize at least some operating actions, to evaluate the curve of the touch force over time, in order with a pulse-type curve of a touch force to recognize an emergency operating action, in particular an emergency movement stop. A pulse-type touch force over the course of time is characterized in that, with an increase exceeding an increase threshold value and/or a time falling below a time threshold value, a touch force exceeding a force threshold value is reached. The corresponding threshold values in such case are to be selected for example so that striking the means of operation 9 is recognized as a pulse-type touch.

Figure 5:
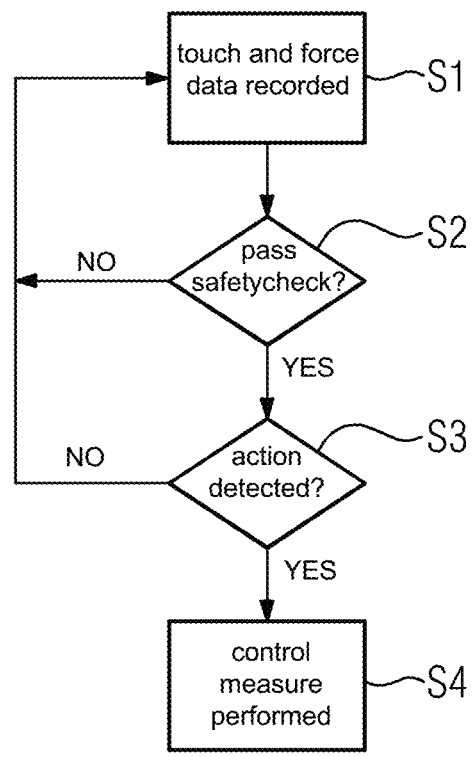
FIG. 5 is a flowchart of a method for operating the imaging device according to an exemplary embodiment.

Finally FIG. 5 shows a flowchart of a method for operating the means of operation 9 on the part of the controller 7. In a step S1 in this method sensor data of the touch sensor 10 and the force sensors 11 is recorded, which in the case of a touch being present, describes the touch position and a touch force, i.e. the strength of the touch. In the case of gestures such sensor data can also be accumulated over time.

In a step S2 various checks are undertaken in respect of operating safety. Thus a check is made on the one hand as to whether the touch position established by the sensors 11 and the touch sensor 10 within the tolerance range match. A minimum touch force represents a further condition, a minimum touch duration a third condition for example. If these conditions are not all fulfilled, the method does not proceed to the recognition of operating actions in step S3. This means that step S3 will only be reached when all conditions are fulfilled in step S2, in order to achieve a single fault safety in this way.

In step S3 the touch positions and touch forces established, where necessary accumulated over time, are then evaluated, in order to detect specific operating actions to which control measures, context-related where necessary, are assigned. If an operating action is detected, the method continues with step S4, in which the correspondingly assigned control measure is then carried out and where necessary display means 18, 19 and/or the display device 14 are activated in order to show that the operating action has been recognized and the control measure carried out.

Although the disclosure has been illustrated and described in greater detail by the preferred exemplary embodiment, the disclosure is not restricted by the disclosed examples and other variations can be derived herefrom by the person skilled in the art without departing from the scope of protection of the disclosure.

References in the specification to "one embodiment," "an embodiment," "an exemplary embodiment," etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described.

The exemplary embodiments described herein are provided for illustrative purposes, and are not limiting. Other exemplary embodiments are possible, and modifications may be made to the exemplary embodiments. Therefore, the specification is not meant to limit the disclosure. Rather, the scope of the disclosure is defined only in accordance with the following claims and their equivalents.

Embodiments may be implemented in hardware (e.g., circuits), firmware, software, or any combination thereof. Embodiments may also be implemented as instructions stored on a machine-readable medium, which may be read and executed by one or more processors. A machine-readable medium may include any mechanism for storing or transmitting information in a form readable by a machine (e.g., a computer). For example, a machine-readable medium may include read only memory (ROM); random access memory (RAM); magnetic disk storage media; optical storage media; flash memory devices; electrical, optical, acoustical or other forms of propagated signals (e.g., carrier waves, infrared signals, digital signals, etc.), and others. Further, firmware, software, routines, instructions may be described herein as performing certain actions. However, it should be appreciated that such descriptions are merely for convenience and that such actions in fact results from computing devices, processors, controllers, or other devices executing the firmware, software, routines, instructions, etc. Further, any of the implementation variations may be carried out by a general purpose computer.

For the purposes of this discussion, the term "processor circuitry" shall be understood to be circuit(s), processor(s), logic, or a combination thereof. A circuit includes an analog circuit, a digital circuit, state machine logic, data processing circuit, other structural electronic hardware, or a combination thereof. A processor includes a microprocessor, a digital signal processor (DSP), central processor (CPU), application-specific instruction set processor (ASIP), graphics and/or image processor, multi-core processor, or other hardware processor. The processor may be "hard-coded" with instructions to perform corresponding function(s) according to aspects described herein. Alternatively, the processor may access an internal and/or external memory to retrieve instructions stored in the memory, which when executed by the processor, perform the corresponding function(s) associated with the processor, and/or one or more functions and/or operations related to the operation of a component having the processor included therein.

In one or more of the exemplary embodiments described herein, the memory is any well-known volatile and/or non-volatile memory, including, for example, read-only memory (ROM), random access memory (RAM), flash memory, a magnetic storage media, an optical disc, erasable programmable read only memory (EPROM), and programmable read only memory (PROM). The memory can be non-removable, removable, or a combination of both.

The invention claimed is:

1. A medical imaging device, comprising:
a movable patient couch;
a controller; and
an operating interface assigned to the controller and configured to control an operation of the movable patient couch, wherein the operating interface includes a touch-sensitive and force-sensitive interface having at least one touch sensor and at least one force sensor configured to measure a strength of a touch.

2. The medical imaging device as claimed in claim 1, wherein:
the operating interface comprises a controller associated with the at least one touch sensor and the at least one force sensor; and/or
the controller is configured to detect at least one possible operating action related to a movement of the movable patient couch in response to:
touch position data being within a tolerance range of matching touch position data of the at least one touch sensor and the at least one force sensor, the at least one force sensor being further configured for touch position measurements, and/or
a minimum touch force and/or a minimum touch duration being exceeded.

3. The medical imaging device as claimed in claim 2, wherein the touch-sensitive and force-sensitive interface comprises a plurality of force sensors installed at different positions, the plurality of force sensors being configured to measure forces for force-sensor-side touch position measurements, and wherein the controller and/or the controller associated with the plurality of force sensors are configured to evaluate the measured forces to establish a touch position and a touch force.

4. The medical imaging device as claimed in claim 3, wherein the controller is configured to:
step-less adapt a control parameter assigned to at least one operating action as a function of the touch force measured for the at least one operating action, and/or
distinguish operating actions based on a touch force and/or a touch duration to recognize a double touch taking place within a period of time as an operating action corresponding to a switching of a mode of operation.

5. The medical imaging device as claimed in claim 1, wherein the controller is configured to evaluate a course of a touch force over time to detect an operating action.

6. The medical imaging device as claimed in claim 5, wherein the controller is configured to detect, based on a touch force exceeding a force threshold value, an emergency operating action including an emergency movement stop, and wherein the touch force exceeding the force threshold value includes a pulse type course of a touch force having an increase exceeding an increase threshold value and/or a time falling below a time threshold value.

7. The medical imaging device as claimed in claim 1, wherein the controller is configured to, on a detection of at least one first operating action, depending on a touch position of the at least one first operating action, define at least two operating areas of an of an operating surface of the touch-sensitive and force-sensitive interface, in which second operating actions assigned to different functionalities are detectable.

8. The medical imaging device as claimed in claim 7, wherein at least two opposite operating areas, of the at least two operating areas, relating to the touch position of the at least one first operating action are assigned to an activation of different directions of a movement and/or directions of an adjustment of the movable patient couch by the controller, wherein a touch force of a second operating action provided for moving the movable patient couch is evaluatable by the controller to establish a speed of a movement and/or a speed of an adjustment of the movable patient couch.

9. The medical imaging device as claimed in claim 7, wherein the controller is configured to evaluate a direction of a drag starting from the touch position after the at least one first operating action to select an operating area.

10. The medical imaging device as claimed in claim 7, wherein the controller is configured to activate a display of the touch-sensitive and force-sensitive interface to display information describing the at least two operating areas.

11. The medical imaging device as claimed in claim 1, wherein the operating interface further comprises at least one acoustic output, a haptic output, and/or an optical display assigned to the touch-sensitive and force-sensitive interface to acknowledge and/or display at least one operating action.

12. The medical imaging device as claimed in claim 11, wherein the optical display is assigned to the movable patient couch and is arranged remotely from the touch-sensitive and force-sensitive interface in a field of vision of a user of the touch-sensitive and force-sensitive interface.

13. The medical imaging device as claimed in claim 1, wherein the touch-sensitive and force-sensitive interface comprises a touchscreen display.

14. The medical imaging device as claimed in claim 1, wherein:
the medical imaging device is a computed tomography device, the touch-sensitive and force-sensitive interface being arranged on a gantry; or
the medical imaging device is a magnetic resonance device, the touch-sensitive and force-sensitive interface being arranged adjacent to a patient receiving area on a main magnet unit.

15. The medical imaging device as claimed in claim 1, further comprising an actuator that is configured to move the movable patient couch.

16. A method for operating a medical imaging device having a movable component and a touch-sensitive and force-sensitive touchscreen display configured to control an operation of the movable component, the method comprising:
measuring, using at least one touch sensor and at least one force sensor of the touch-sensitive and force-sensitive touchscreen display, a strength of a touch input on the touch-sensitive and force-sensitive touchscreen display; and
controlling a movement of the movable component based on the measuring.

17. The method as claimed in claim 16, wherein the movable component is a patient couch, a light, an imaging device, or an air conditioner.

18. The method as claimed in claim 16, wherein the medical imaging device is a computed tomography device and/or a magnetic resonance device.

19. A non-transitory computer-readable storage medium with an executable computer program stored thereon, that when executed, instructs a processor to perform the method of claim 16.

* * * * *